United States Patent
Hall et al.

(10) Patent No.: US 10,273,674 B2
(45) Date of Patent: Apr. 30, 2019

(54) TOILET BOWL FOR SEPARATING FECAL MATTER AND URINE FOR COLLECTION AND ANALYSIS

(71) Applicants: David R. Hall, Provo, UT (US); Daryl Wise, Provo, UT (US); John Christensen, Bluffdale, UT (US); Joe Fox, Spanish Fork, UT (US); Matthew Goodson, Yucaipa, CA (US)

(72) Inventors: David R. Hall, Provo, UT (US); Daryl Wise, Provo, UT (US); John Christensen, Bluffdale, UT (US); Joe Fox, Spanish Fork, UT (US); Matthew Goodson, Yucaipa, CA (US)

( * ) Notice: Subject to any disclaimer, the term of this patent is extended or adjusted under 35 U.S.C. 154(b) by 12 days.

(21) Appl. No.: 15/632,807

(22) Filed: Jun. 26, 2017

(65) Prior Publication Data
US 2018/0371735 A1    Dec. 27, 2018

(51) Int. Cl.
| | | |
|---|---|---|
| *A61B 10/00* | (2006.01) | |
| *E03D 11/13* | (2006.01) | |
| *A61B 5/1455* | (2006.01) | |
| *G01N 33/483* | (2006.01) | |
| *G01N 33/487* | (2006.01) | |
| *G01N 33/493* | (2006.01) | |

(52) U.S. Cl.
CPC ........... *E03D 11/13* (2013.01); *A61B 5/1455* (2013.01); *G01N 33/4833* (2013.01); *G01N 33/48792* (2013.01); *G01N 33/493* (2013.01); *A61B 10/007* (2013.01); *A61B 10/0038* (2013.01)

(58) Field of Classification Search
CPC ............................. A61B 5/1455; E03D 11/13
USPC ................. 4/318–319, 144.1–144.2, 420; 600/573–584
See application file for complete search history.

(56) References Cited

U.S. PATENT DOCUMENTS

| | | | | |
|---|---|---|---|---|
| 4,276,889 A | * | 7/1981 | Kuntz ................. | G01N 1/10 4/144.1 |
| 4,860,767 A | * | 8/1989 | Maekawa .............. | E03D 11/00 600/573 |
| 6,087,182 A | * | 7/2000 | Jeng ...................... | G01N 21/05 356/72 |
| 2007/0130678 A1 | * | 6/2007 | Ikeda .................... | A47K 11/02 4/434 |
| 2010/0205727 A1 | * | 8/2010 | Muhlhausen .......... | E03D 9/032 4/223 |

\* cited by examiner

*Primary Examiner* — Christine J Skubinna

(57) ABSTRACT

The toilet bowl separately collects urine and feces for analysis or use in a composting device, waste digester, or to reclaim water. The toilet bowl includes a toilet bowl wall. Urine flows down the toilet bowl wall into a channel for collection. The channel surrounds an aperture into which feces may be deposited. Consequently, urine and feces are kept separate during collection. Both the channel and the aperture may be connected to conduits which may transmit material into analytical devices. The conduits may transmit material into digesters in appropriate amounts including controlling the amount of liquid added to solid material. Collected urine may be stored for water reclamation. Sensors may confirm the absence of fecal matter in collected urine or detect contamination. After separate analysis, feces and urine may be combined through connecting conduits then disposed of in the sewer system or sent to a composting device or waste digester.

13 Claims, 8 Drawing Sheets

TOILET BOWL FOR SEPARATING FECAL MATTER AND URINE FOR COLLECTION AND ANALYSIS

BACKGROUND

Field of the Invention

This disclosure relates to methods of collecting and analyzing biological samples and biological waste.

Background of the Invention

Collecting fecal and urine samples according to traditional methods may be a messy, hazardous, inconvenient, and emotionally uncomfortable for the individual providing the sample. Typically, it is important to keep fecal and urine samples separate. A device is needed which may collect fecal and urine samples for storage or analysis which is convenient, discrete, sanitary, automated, and capable of preventing the cross-contamination of the feces and urine.

BRIEF SUMMARY OF THE INVENTION

The disclosed toilet bowl separately collects feces and urine for purposes that include analysis to gather health and diagnostic data, water reclamation, composting, and use in digesters. The toilet bowl may include a toilet bowl wall that may slant downward toward a channel. The channel may surround an aperture approximately in the center of the inside of the toilet bowl. The channel may comprise an inner channel wall and an outer channel wall. The lower part of the toilet bowl wall may define the outer channel wall and the inner channel wall may define the aperture.

A user may deposit urine anywhere throughout the toilet bowl except for the aperture and the urine will flow into the channel for collection. Feces may be deposited into the aperture. Consequently, urine is collected in the channel and feces is separately collected through the aperture.

A urine conduit may be in fluid communication with the channel and transmit urine from the channel to a urinalysis device, a storage container, a composting device, a waste digester, or combination thereof. A fecal conduit may be in communication with the aperture and transmit feces into an analytical device, a storage container, a composting device, a waste digester, or combination thereof. A urine return conduit may return urine from the urine conduit back into the fecal conduit. For example, urine, feces, or both may be analyzed using analytical devices. The feces may continue passage through the fecal conduit and the urine may pass from the urine conduit into the urine return conduit which feeds into the fecal conduit. Typically, the connection between the urine return conduit and the fecal conduit will be distal to any analytical devices. Consequently, both forms of waste may be combined after their analysis. Then the combined waste may proceed to the sewer system, composting device, or waste digester.

The inner channel wall, the outer channel wall, or both may slant away from vertical to prevent cross-contamination of feces and urine during collection. In some embodiments, the slant is angled away from the aperture and toward the toilet bowl wall. Some embodiments further include a rim at the top of one or both of the channel walls. The rim may provide an additional barrier to cross-contamination.

The top of the inner channel wall, outer channel wall, or both may include one or more sensors. The sensors may include capacitive sensors. These sensors may detect when material passes over the channel wall either by feces passing from the aperture into the channel or by urine overflow passing from the channel into the aperture.

Optical sensors may be present which may detect cross-contamination. The optical sensor may include two optical windows through which a light source emits light of a defined wavelength or range of wavelengths. The two optical windows may be present on an inner channel wall and an outer channel wall and the light may be directed across the channel. In another embodiment, the two optical windows are on opposite sides of the urine conduit and the light is directed across the urine conduit. In either embodiment, the light transmitted out of the second optical window may be detected by a spectrometer. Contaminants in the urine alter the spectra and are identified by the detected spectra.

DETAILED DESCRIPTION OF THE INVENTION

Figure 1:
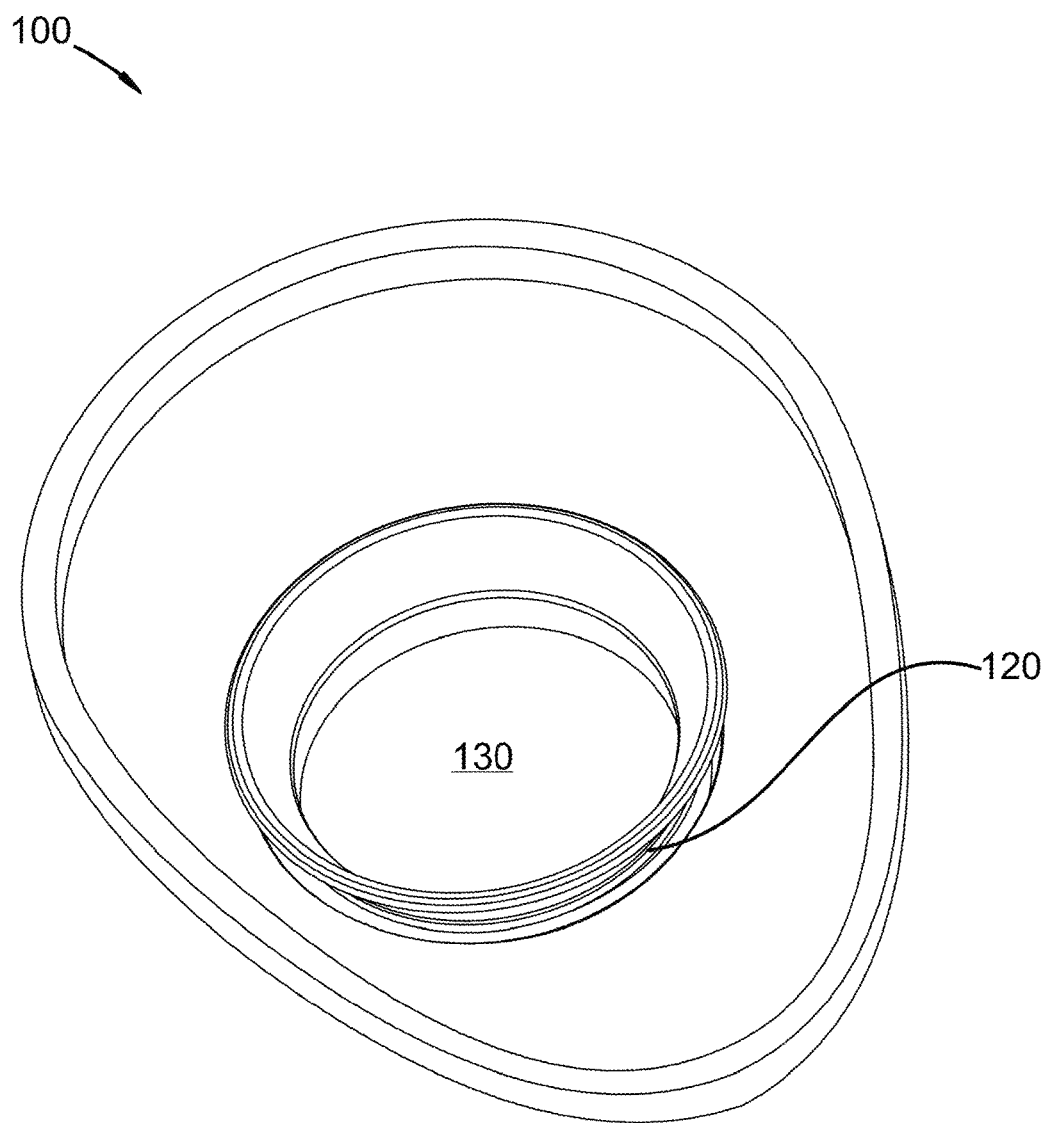
FIG. 1 illustrates an aerial view of an embodiment of the disclosed toilet bowl.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a toilet bowl which makes separate collection of urine and feces convenient, discreet, sanitary, and automated. The toilet bowl prevents cross-contamination of urine and feces during collection. The separate urine and fecal samples may be subjected to analysis to gather data that may be used to assess a user's health and provide a diagnosis. In addition, the disclosed toilet bowl may provide greater flexibility for composting toilets/waste digesters, allowing moisture content to be more carefully controlled by separating out the urine, which could be treated separately or added to the solids in precise quantities.

The toilet bowl may include a bowl which may include a toilet bowl wall that is slanted at an angle. Urine which encounters the toilet bowl wall may flow down the toilet bowl wall using the force of gravity. The bowl may include a channel defined by an inner channel wall and an outer channel wall. The outer channel wall may be a lower section of the toilet bowl wall. The toilet bowl wall may slant toward the channel. Thus, urine flowing down the toilet bowl wall may flow into the channel.

The channel may surround an aperture. In some embodiments, the inner channel wall may define the aperture. The inner channel wall may form an inverted truncated cone. Feces may be deposited into the aperture while urine is separately collected into the channel. By placing the channel around the aperture, a user may dispense urine anywhere in the toilet bowl other than directly into the aperture and still maintain the separate collection of urine and feces.

In some embodiments, the inner and outer channel walls may be inclined at an angle. Consequently, the channel may be inclined at an angle. In some embodiments, the channel is angled away from the aperture, a design which may inhibit feces from crossing over the inner channel wall and into the channel which is reserved for urine.

The aperture may be surrounded by a rim. The rim may extend from the inner channel wall, the outer channel wall, or both the inner channel wall and the outer channel wall. The rim may provide a further barrier between urine in the channel and feces being deposited into the aperture.

In some embodiments, one or more sensors may be disposed on the rim or on an upper edge of the inner channel wall, the outer channel wall, or both the inner channel wall and the outer channel wall. In some embodiments, the sensors are capacitive sensors. The sensors may sense when material passes over the inner or outer channel wall thus indicating cross-contamination of urine and feces.

In some embodiments, the channel is in fluid connection with a urine conduit. The urine conduit may transfer urine from the channel, either through gravitational force or using a pump. In an example, the pump is a peristaltic pump or other pump known in the art. The urine conduit may transmit the urine from the channel into a urinalysis device. The urinalysis device may analyze the urine for use in assessing a user's health or providing a diagnosis. The urine conduit may transmit urine to a composting device or waste digester to control the amount of moisture added to the system.

In addition, or in the alternative, the toilet bowl may include a fecal conduit. The fecal conduit may be connected to the aperture where feces is deposited. The fecal conduit may transmit feces into an analytical device for assessing a user's health or providing a diagnosis. In some embodiments, the fecal conduit may transmit feces into a composting or waste digester apparatus.

Some embodiments may further include a urine return conduit. After traveling from the channel into a urinalysis device, the urine may leave the urinalysis device through the urine return conduit. The urine return conduit may then connect to the fecal conduit. In embodiments which include an analytical device for analyzing feces, the urine return conduit may connect to the fecal conduit at a position that is distal to the analytical device. Consequently, the urine and feces may be combined after their analyses is complete. Be recombining the urine and feces, both solid and liquid waste may be simultaneously disposed of into the sewer system, composting device, or waste digester. In addition, the rate of urine flow through the urine return conduit may be regulated to control the amount of liquid added to solid waste destined for a composting or waste digester apparatus. For the same purpose, the urine conduit may be in fluid communication with a urine storage container. The urine may then be distributed into a composting or waste digester apparatus in appropriate amounts at a later time. The water in the urine may also be reclaimed from the urine storage container for subsequent use.

It may be useful to thoroughly cleanse the toilet bowl between uses, particularly when waste is being analyzed for health and diagnostic purposes. Accordingly, some embodiments may include one or more flush water dispensers for dispensing flush water down the toilet bowl wall, into the channel, and out into the sewer. In some embodiments, the flush water dispensers are disposed on the toilet bowl wall. Residual urine may be washed away with the flush water between uses. In addition, or in the alternative, some embodiments may include cleansing agent dispensers which may dispense cleansing agents on the toilet bowl wall. In some embodiments, the cleansing agent dispensers are disposed on the toilet bowl wall. The cleansing agents may flow down the toilet bowl wall into the channel, and out into the sewer thus cleansing the channel. The cleansing agent dispensers may dispense surfactants and/or antimicrobial substances. In embodiment which include both flush water dispensers and cleansing agent dispensers, the flush water from the flush water dispensers may provide a rinse to remove cleansing agent between uses.

While the instant design inhibits cross-contamination of urine and feces during collection, it may be useful to include sensors which detect cross-contamination and confirm the lack thereof. Accordingly, some embodiments may include optical sensors which detect the presence of feces in collected urine. In some embodiments, the optical sensor may include one or more optical windows disposed on the urine conduit. A light source may transmit light of a defined wavelength or range of wavelengths through a first optical window, across the width of the urine conduit, and out through a second optical window positioned across the conduit from the first optical window. A spectrometer may detect a spectrum of light transmitted through the second optical window. The contents of the urine conduit will impact the detected spectrum and fecal contamination in the urine may be identified.

Other embodiments may include an optical sensor which includes two optical windows disposed within the channel. In an example, a first optical window may be disposed within the outer channel wall and a second optical window may be disposed within the inner channel wall directly across the channel from the first optical window. A light source may transmit light of a defined wavelength or range of wavelengths through the first optical window, across the width of the channel, and out through the second optical window. A spectrometer may detect a spectrum of light transmitted out through the second optical window. The contents of the channel will impact the detected spectrum and fecal contamination in the urine may be identified.

Referring now to the drawings, FIG. 1 illustrates an aerial view of an embodiment of toilet bowl 100. Toilet bowl 100 includes toilet bowl wall 110 which slants down at an angle toward channel 120. Channel 120 surrounds aperture 130.

Figure 2:
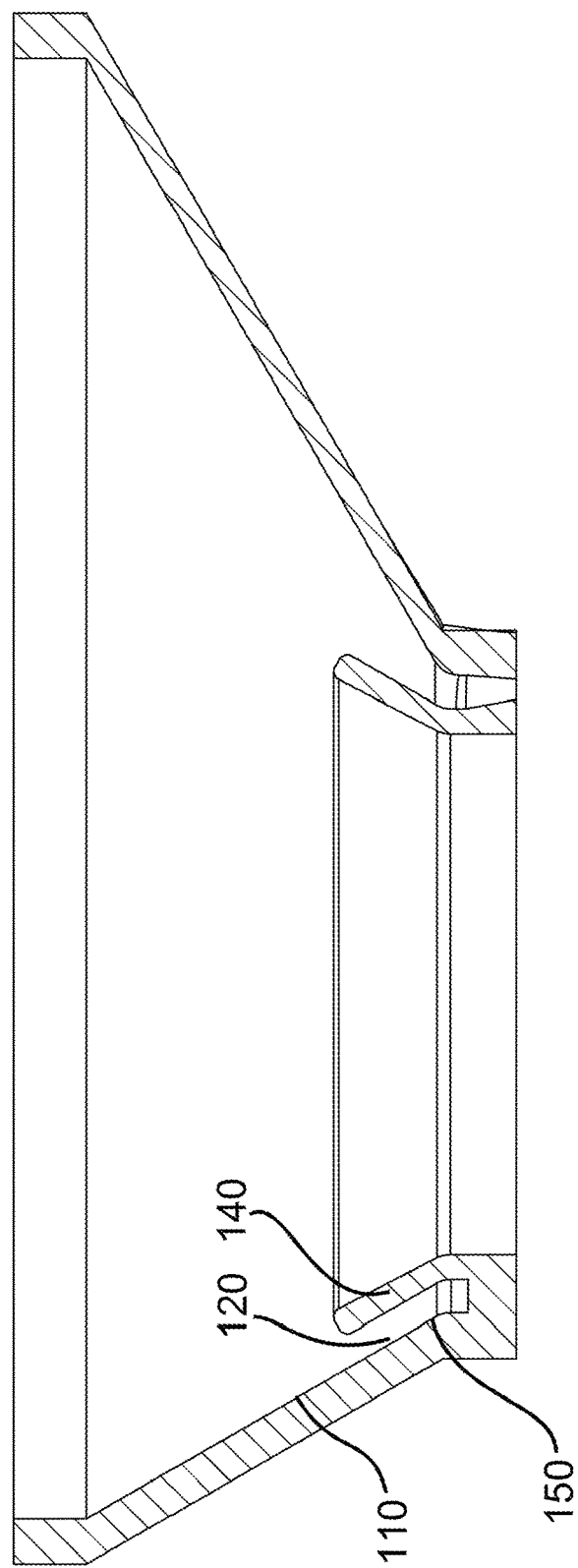
FIG. 2 illustrates a cross-sectional view of an embodiment of the disclosed toilet bowl.

FIG. 2 illustrates a cross-sectional view of toilet bowl 100 of FIG. 1. Toilet bowl wall 110 slants down at an angle toward channel 120. Inner channel wall 140 surrounds the aperture and outer channel wall 150 is formed from a lower section of toilet bowl wall 110. The inner channel wall 140 may form an inverted truncated cone.

Figure 3:
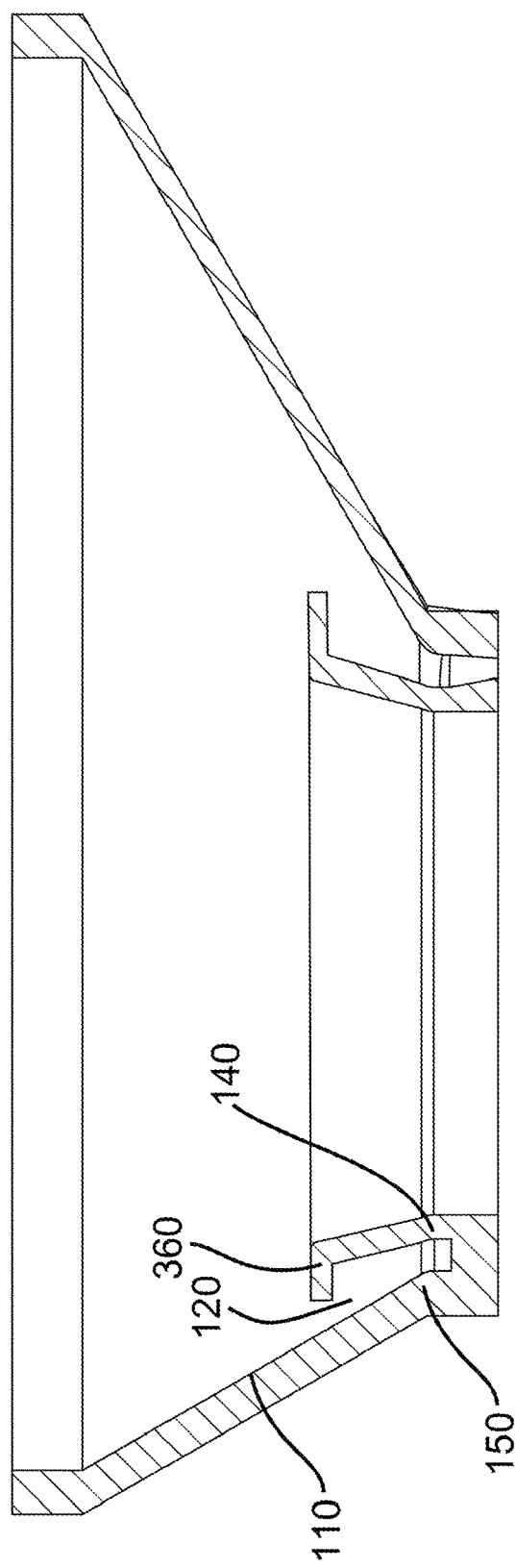
FIG. 3 illustrates a cross-sectional view of an embodiment of the disclosed toilet bowl which includes a rim surrounding the aperture.

FIG. 3 illustrates another embodiment of the disclosed toilet bowl. The embodiment of FIG. 3 includes toilet bowl wall 110, inner channel wall 140 and outer channel wall 150. The inner channel wall 140 may form an inverted truncated cone. However, unlike the embodiment of FIG. 1, rim 360 is disposed at the top of inner channel wall 140. Rim 360 surrounds the aperture and provides a barrier between urine which may run down the inner surface of toilet bowl wall 110 into channel 120 and feces which may be deposited in the aperture.

Figure 4:
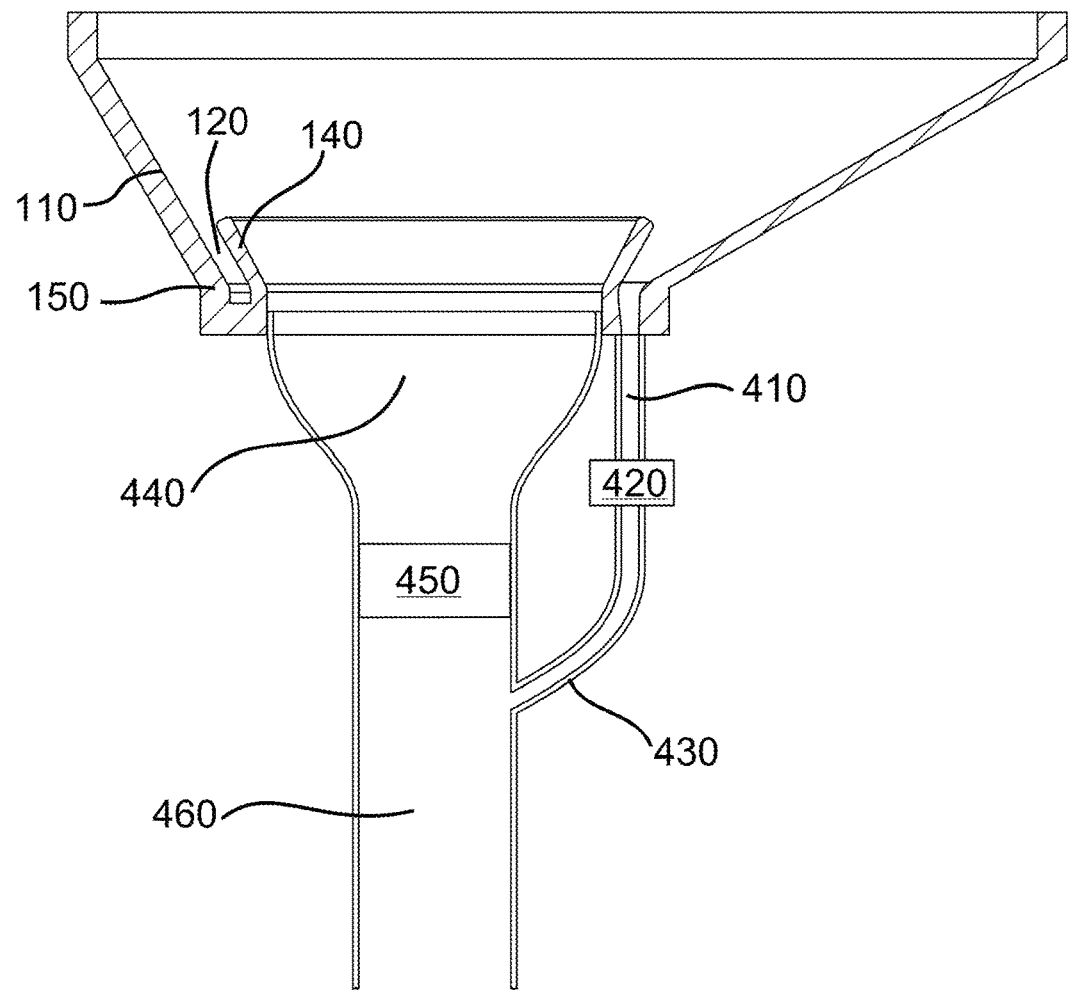
FIG. 4 illustrates a cross-sectional view of an embodiment of the disclosed toilet bowl in which urine is recombined with feces after analysis.

FIG. 4 illustrates yet another embodiment of the disclosed toilet bowl which includes urine conduit 410. Urine conduit 410 is in fluid communication with channel 120. Urine collected in channel 120 may travel through urine conduit 410 into urinalysis device 420. Feces may be deposited into the aperture and travel through fecal conduit 450 into analytical device 450. The urine sample may be analyzed by urinalysis device 420 and the feces may be analyzed by analytical device 450. The urine may then travel from urinalysis device 420, through urine return conduit 430, into a distal section 460 of fecal conduit 440. Distal section 460 of fecal conduit 450 may be distal to analytical device 450. Thus, after both urine and feces have been analyzed with their respective devices, they are combined in distal section 460 of fecal conduit 450 and directed toward the sewer system, composting device, or waste digester as indicated by the arrow.

Figure 5:
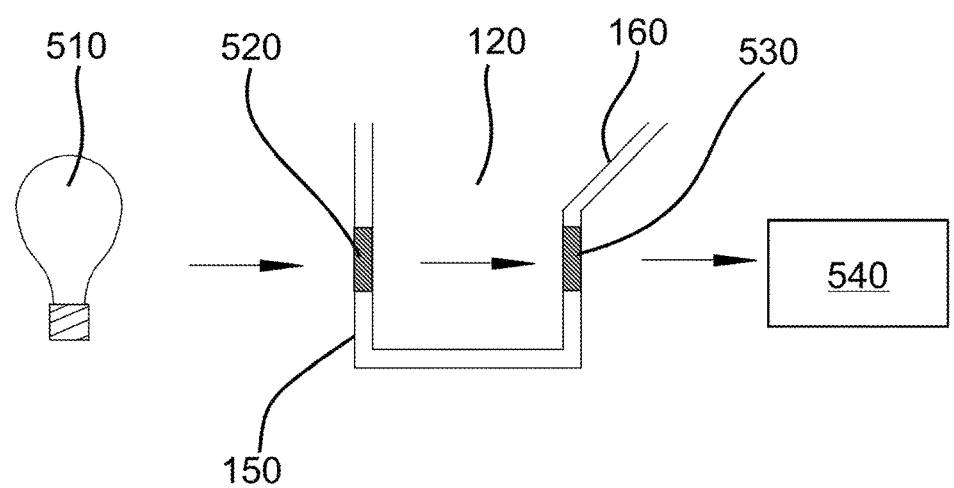
FIG. 5 illustrates a cross-sectional view of an embodiment including an optical sensor within the channel.

FIG. 5 illustrates a close-up cross-sectional view of an embodiment of channel 120 which includes an optical sensor. Light source 510 sends light of a defined wavelength or range of wavelengths through optical window 520 which is disposed within inner channel wall 150. The light passes through the contents of channel 120 and exits through optical window 530. Spectrometer 540 detects the wavelengths of the light exiting optical window 530. This may serve two purposes: urine may be analyzed for health purposes and fecal contamination may be detected by analysis of the detected spectrum.

Figure 6:
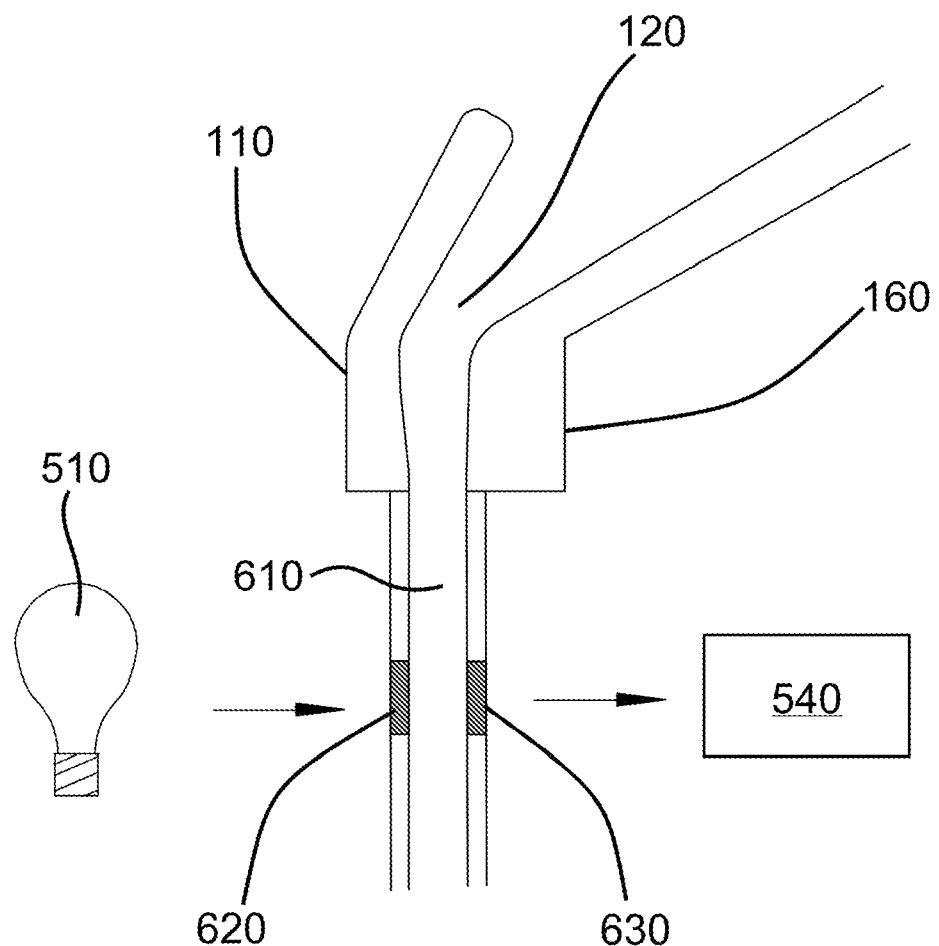
FIG. 6. illustrates a cross-sectional view of an embodiment including an optical sensor within the urine conduit.

FIG. 6 illustrates a close-up cross-sectional view of an embodiment of channel 120 that includes urine conduit 610 and an optical sensor in urine conduit 610. Light source 510 sends light of a defined wavelength or range of wavelengths through optical window 620 in urine conduit 610. The light passes through the contents of urine conduit 610 and exits through optical window 630. Spectrometer 540 detects the wavelengths of the light exiting optical window 630. Similar to the embodiment of FIG. 5, this process may both analyze urine for health purposes and assess for fecal contamination using the detected spectrum.

Figure 7:
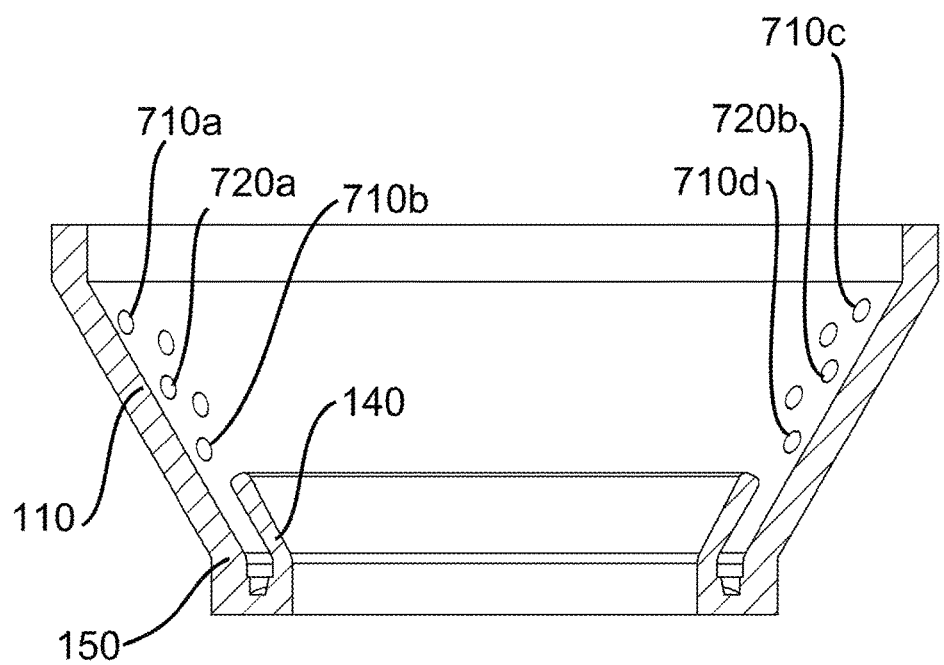
FIG. 7 illustrates a cross-sectional view of an embodiment including flush water dispensers and cleansing agent dispensers.

FIG. 7 illustrates a cross-sectional view of an embodiment of the disclosed toilet bowl which includes flush water dispensers 710a, 710b, 710c, and 710d. Flush water dispensers 710a-d dispense flush water which is directed down the sides of toilet bowl wall 110 thus washing excess urine into channel 120 which eventually leads to the sewer system in between use. The embodiment of FIG. 7 also includes cleansing agent dispensers 720a and 720b which dispense one or more cleansing agents to further cleans toilet bowl wall 110 and channel 120.

Figure 8:
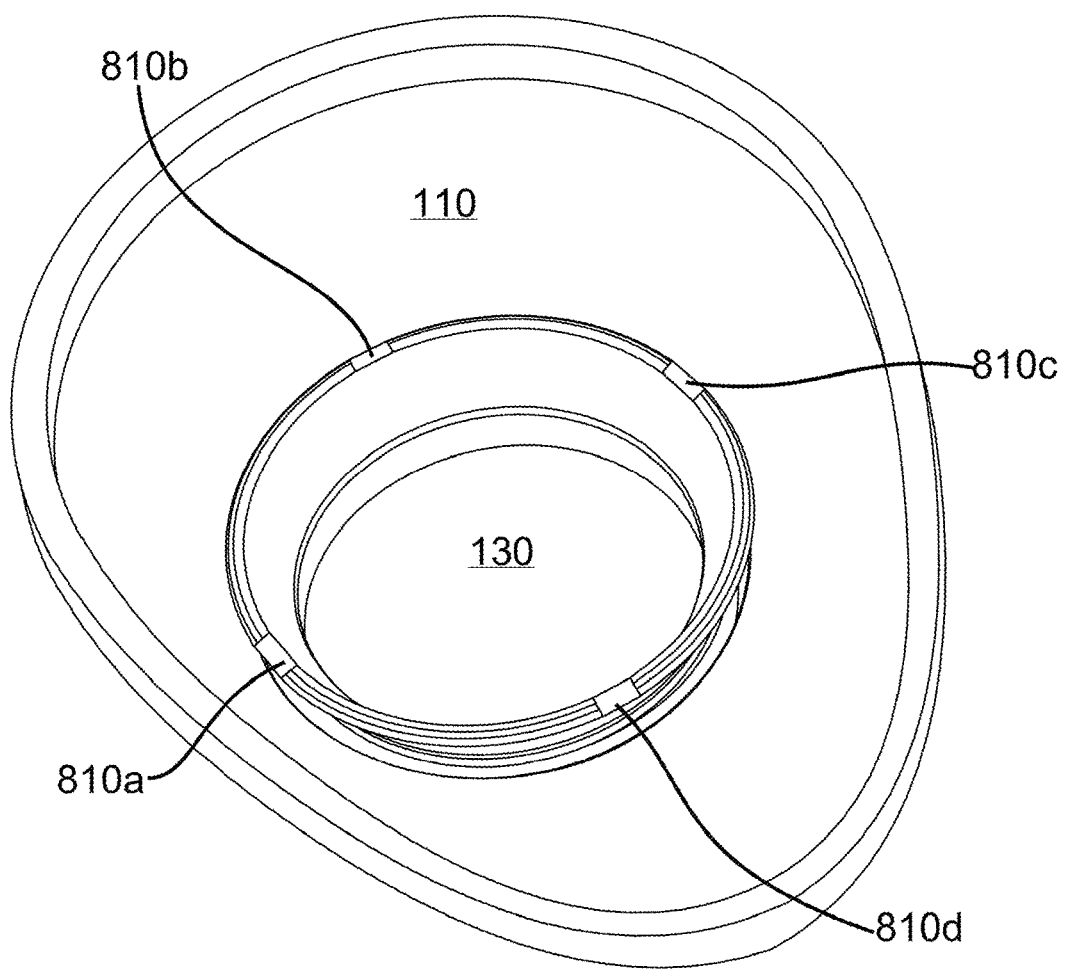
FIG. 8 illustrates an aerial view of an embodiment including capacitive sensors on the rim surrounding the aperture.

FIG. 8 illustrates an aerial view of an embodiment of the disclosed toilet bowl which includes sensors 810a, 810b, 810c, and 810d on the upper edge of inner channel wall surrounding aperture 130. Sensors 810a-d may detect material crossing over the inner channel wall causing cross-contamination of the urine and feces. Sensors 810a-d may detect urine flowing over the inner channel wall into aperture 130 which is intended to collect feces. Alternatively, sensors 810a-d may detect feces crossing the inner channel wall into the channel which is intended to collect urine.

While specific embodiments have been described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A toilet bowl for separately collecting urine and feces comprising:
   a. a bowl, the bowl comprising:
      i. a toilet bowl wall;
      ii. a channel, the channel comprising an inner and an outer channel wall, wherein toilet bowl wall surrounds the channel; and
      iii. an aperture, wherein the inner channel wall defines the aperture;
   b. a fecal conduit, wherein the fecal conduit is in communication with the aperture;
   c. a urine conduit, wherein the urine conduit is in fluid communication with the channel;
   d. a urinalysis device, wherein the urinalysis device is in fluid communication with the urine conduit; and
   e. a urine return conduit,
      i. wherein the urinalysis device is disposed between the urine conduit and the urine return conduit;
      ii. wherein the urine return conduit is in communication with the fecal conduit at a point where urine return conduit and the fecal conduit combine; and
      iii. wherein the fecal conduit is in communication with a sewer, composting device, or waste digester at a point which is distal to the point where urine return conduit and the fecal conduit combine.

2. The toilet bowl of claim 1, wherein a lower section of the toilet bowl wall defines the outer channel wall.

3. The toilet bowl of claim 1, wherein the inner channel wall, the outer channel wall, or both the inner and outer channel walls comprise a rim.

4. The toilet bowl of claim 3, further comprising at least one sensor, wherein the at least one sensor is disposed on the rim.

5. The toilet bowl of claim 4, wherein at least one of the at least one sensors comprises a capacitive sensor.

6. The toilet bowl of claim 1, wherein the inner channel wall, the outer channel wall, or both the inner and outer channel walls are inclined at a first angle.

7. The toilet bowl of claim 6, wherein the first angle is directed away from the aperture.

8. The toilet bowl of claim 1, wherein the toilet bowl wall is inclined at a second angle, and wherein the second angle is between about 40 degrees and about 70 degrees from a horizontal plane.

9. The toilet bowl of clam 1, further comprising:
   a. an optical sensor;
   b. a spectrometer; and
   c. a first and a second optical window, wherein the first optical window is disposed within the inner channel wall and the second optical window is disposed within the outer channel wall, and wherein the spectrometer measures a spectrum of light transmitted out of the channel through the second optical window.

10. The toilet bowl of claim 1, wherein the fecal conduit is in communication with an analytical device capable of analyzing feces.

11. The toilet bowl of claim 1, further comprising one or more flush water dispensers, wherein the one or more flush water dispensers dispense flush water onto the toilet bowl wall.

12. The toilet bowl of claim 1, further comprising one or more cleansing agent dispensers, wherein the one or more cleansing agent dispensers dispense one or more cleansing agents onto the toilet bowl wall.

13. The toilet bowl of claim 1, wherein the inner channel wall forms an inverted truncated cone.

* * * * *